(12) United States Patent
Taralp (10) Patent No.: US 8,716,219 B2
(45) Date of Patent: May 6, 2014

(54) CROSSLINKED PROTEIN NANOCRYSTALS, CROSSLINKED PROTEIN NANOAGGREGATES AND METHOD OF PREPARATION THEREOF

(75) Inventor: Alpay Taralp, Istanbul (TR)

(73) Assignee: Sabanci University, Istanbul (TR)

( * ) Notice: Subject to any disclaimer, the term of this patent is extended or adjusted under 35 U.S.C. 154(b) by 648 days.

(21) Appl. No.: 12/831,232

(22) Filed: Jul. 6, 2010

(65) Prior Publication Data

US 2011/0008455 A1 Jan. 13, 2011

Related U.S. Application Data

(60) Provisional application No. 61/223,691, filed on Jul. 7, 2009.

(51) Int. Cl.
*C07K 14/00* (2006.01)
*A61K 9/14* (2006.01)

(52) U.S. Cl.
USPC ............................ 514/2; 424/499; 977/773

(58) Field of Classification Search
None
See application file for complete search history.

(56) References Cited

U.S. PATENT DOCUMENTS

| | | | |
|---|---|---|---|
| 4,001,401 A | 1/1977 | Bonsen et al. | |
| 6,303,150 B1 * | 10/2001 | Perrier et al. | 424/491 |
| 2008/0296231 A1 | 12/2008 | Schoevaart et al. | |
| 2009/0004278 A1 | 1/2009 | Aimi et al. | |

OTHER PUBLICATIONS

Pepin and Lortie, "Influence of water activity on the enantioselective esterification of (R,S)-ibuprofen by crosslinked crystals of *Candida antarctica* Lipase B in organic solvent media", Biotechnology and Bioengineering 75(5): 559-562 (Dec. 2001).*
Balthasar et al., "Preparation and characterisation of antibody modified gelatin nanoparticles as drug carrier system for uptake in lymphocytes", Biomaterials 26: 2723-2732 (2005).*
F D'Agnillo and TMS Chang, "Polyhemoglobin-superoxide dismutase-catalase as a blood substitute with antioxidant properties" Nature Biotechnology, 16, 667-671, 1998.
Robert Winslow, Blood Substitutes, Chp. 38, Elsevier, London, GB, 2006.
J Lee et al., "Simple Synthesis of Hierarchically Ordered Mesocellular Mesoporous Silica Materials Hosting Crosslinked Enzyme Aggregates", Small 1, 744-753, 2005.
BL Simons et al., "Covalent cross-linking of proteins without chemical reagents", Protein Science 11, 1558-1564, 2002.
RW Martin and KW Zilm, "Preparation of protein nanocrystals and their characterization by solid state NMR", Journal of Magnetic Resonance, 165, 162-174, 2003.
JC Falkner et al., "Generation of sizecontrolled, submicrometer protein crystals", Chem. Mater. 17, 2679-2686, 2005.
K Zhang et al., "Stopped-flow spectrophotometric determination of $H_2O_2$ with Hb as catalyst", Talanta 51, 179-186, 2000.

* cited by examiner

*Primary Examiner* — Anand Desai
(74) *Attorney, Agent, or Firm* — Intellectual Property Law Group LLP (57) ABSTRACT

This invention relates to crosslinked protein nanoparticles and a method for producing the same. The method comprises the preparation and nanonization (i.e., size reduction to the nanoscale) of protein nanoparticle precursor materials—i.e., crosslinked proteins of the micron or greater size—via mechanical or hydrodynamic shear, mechanical crushing, sonic cavitation and/or hydrodynamic cavitation.

21 Claims, 5 Drawing Sheets

CROSSLINKED PROTEIN NANOCRYSTALS, CROSSLINKED PROTEIN NANOAGGREGATES AND METHOD OF PREPARATION THEREOF

CROSS REFERENCE TO RELATED APPLICATIONS

This application claims priority to provisional U.S. Application No. 61/223,691, filed on Jul. 7, 2009, which is incorporated herein by reference in its entirety.

BACKGROUND OF THE INVENTION

1. Field of Invention

This invention relates to crosslinked protein nanoparticles and a nanonization method for producing crosslinked protein nanoparticles.

2. Background

Protein-based applications, principally but not necessarily restricted to the use of enzymes, antibodies, receptors, hormones, and structural proteins, are well established in the biotechnology, biomedicine, pharmacy, biomaterial and cosmetics industries. Some common problems related to the application of individual proteins, such as short half-life, poor stability, poor recoverability, narrow scope of use, high cost, hydrolytic instability and poor bioavailability have been addressed, at least in part, by the use of crosslinked protein crystals and aggregates. Said crystals and aggregates, comprising of micron or greater sized particles, have provided for structurally and chemically robust, long-lived material, which have bypassed many limitations common to individual proteins and thereby ameliorated some major problems. Still, their micron and greater size has introduced an assortment of problems foreign to individual proteins, such as mass transport limitations, reduced access to catalytic centers, restricted catalytic turnover due to crosslinking, and poor bioabsorptivity. In some cases, high costs have also prevailed, despite the reusability of said preparations.

There is also a continuing drive to optimize the bioactivity, stability, shelf-life, scope of use, and bioavailability of protein products by the implementation of nanotechnology. Collectively termed herein as protein nanoparticles (i.e., protein material with a cross-sectional length under one micron in every dimension), the few examples reported to date consist of protein nanoaggregates (i.e., non-crystalline protein nanoclusters, comprising of dimers and even higher associations), and protein nanocrystals (i.e., crystalline protein nanoparticles). The preparation and utilization of novel nano-sized protein aggregates and crystals, especially of the crosslinked type, describes an area of study, touting limited success.

In view of the limited availability, scope and production constraints of protein-based products, a demand exists to realize materials, such as novel crosslinked protein nanoparticles. Analogously, a demand also exists to establish convenient preparative methodologies so that said crosslinked protein nanoparticles can be better utilized, in general, to address much of the current problems of industry and medicine. Unfortunately, the development and preparation of new crosslinked protein nanoparticles has been slowed by technical problems, for which general and facile solutions are lacking. The physico-chemical attributes notably present in nanoscale materials, such as inherently high surface energy and reactivity, is one factor that underlies these difficulties. Among the established protein-based products, only bottom-up strategies, in which individual native-state proteins are brought together, forming larger associations, have been utilized to prepare crosslinked protein nanoparticles. In contrast, no approach has reported the preparation of crosslinked protein nanoparticles by employing physical size reduction methods (i.e., top-down approaches) on larger crosslinked protein materials. Indeed, nanonization (i.e., size reduction of larger material to the nanoscale) or nanofragmentation (i.e., fragmentation of larger material to yield nanosized fragments or "nanofragments") remains to be tested on crosslinked proteins. The commonly professed belief that proteins are easily harmed by "unnatural" process conditions is one factor that has discouraged an earlier assessment of the merit of size reduction. In addition, the act of fragmenting soft materials— implying protein-based materials—is known to become increasingly difficult as the particle size diminishes. This common perception has likely served as a second discouraging factor.

SUMMARY OF THE INVENTION

In the invention, the challenges of preparing crosslinked protein nanoparticles are resolved by applying a physical size reduction approach to a crosslinked, micron-or-greater sized protein material (hereafter termed the precursor material). Such an approach yields robust protein-based nanoparticulate materials of controllable size. As well, it bypasses the established or plausible technical problems related to the direct preparation of crosslinked protein associations from individual proteins in solution. The resultant crosslinked proteins, which are nanofragments or nanofragmentation products of said precursor material, form an entirely new class of nanoscale crosslinked protein products, termed herein as crosslinked protein nanoparticles (i.e., crosslinked protein nanocrystals and crosslinked protein nanoaggregates with a cross-sectional length of less than one micron in each dimension).

The prior art examples, which may inadvertently be misconstrued as reporting comparable products (i.e., on the grounds of similar terminology, e.g., protein nanoparticle), actually describe another class of crosslinked protein products. These products are prepared from individual, native proteins (i.e., noncrosslinked precursors), which clearly depict a different source of precursor when compared against the invention. Again, the product of the invention is a nanofragment of a crosslinked and comparatively much larger structure. Said crosslinked nanoparticles of the invention display high bioavailability in that they are readily internalized into cells, by any number of conventional means known to medical practitioners, and they are longer-lived in the body compared to individual proteins. In addition, these nanoparticles are ingestible as they have remarkable hydrolytic stability, and hence they offer new avenues for absorption into the body, such as through the GALT (gut-associated lymphoid tissue) system. Said nanoparticles display high bioactivities in view of their favorable surface and diffusion/mass-transport characteristics, and improved operational stability due to the crosslinking effect, which is known to those experienced in the field.

The precursor material of crosslinked protein nanoparticles may be obtained commercially. Alternatively, the methods to prepare said crosslinked protein nanoparticle precursor are available to anyone familiar in the art. Said precursor material is prepared in two steps. Firstly, a suitable solvent/antisolvent precipitation or lyophilization method is implemented on the target protein, forming micron or greater sized protein aggregates, or a crystallization method is implemented, forming micron or greater sized protein crystals; subsequently, any conventional chemical crosslinking method (i.e., chemical reagent-promoted, chemically reactive linker-promoted and/or enzyme-promoted) or dehydrothermal crosslinking method (i.e., heat-promoted condensation) is implemented, forming the covalently crosslinked protein material (i.e., the precursor material of the invention). To prepare the crosslinked nanoparticle product, said precursor is physically reduced in size, directly yielding the corresponding crosslinked protein nanoaggregates or nanocrystals, and bypassing any problems typically associated with the established bottom-up approaches.

Accordingly, the present invention provides for a covalently crosslinked protein nanoparticle, sized 10-999 nm and preferably 50-200 nm, suitable for enabling biotechnology, cosmetic, pharmaceutical and biomedical applications, characterized in that said nanoparticle, which comprises of one or more types of protein and at least one type of zero-or-greater length inter-protein crosslink, is obtained as the nanofragmentation product of a compositionally equivalent or near-equivalent precursor material, having a minimum length, in each dimension, of one micron.

Another embodiment of the present invention relates to a surprisingly simple method to prepare a crosslinked protein nanoparticle by nanonizing (i.e., reducing the physical size to the nanoscale) the precursor material (i.e., a crosslinked micron-or-larger sized protein aggregate or crystal), which is purchased or readily prepared in-house.

Another embodiment the present invention relates to the use of a crosslinked protein nanoparticle, produced by the defined method, for improved performance via any topical or systemic administrative route including transdermal, oral (and eventually GALT), transmucosal (e.g., buccal, sublingual), inhalation, and injection (e.g., intraperitoneal, intramuscular, subcutaneous, intrathecal, intraparenchymal, and infusion).

Another embodiment the present invention relates to the use of a crosslinked protein nanoparticle, produced by the defined method, to restore the metabolic imbalance arising from any one of the known lysosomal storage disorders.

Shown below, crosslinked protein associations have been previously obtained by physically assembling individual protein units, and simultaneously or subsequently invoking a chemical, enzymatic or dehydrothermal crosslinking method. The act of crosslinking has been explored intensively and its role has varied. For instance, in many cases protein associations, forming nanoaggregates, have not been a spontaneous or predictable process. Accordingly, covalent crosslinking methods have been used to physically drive and to fine-tune the assembly of protein nanoaggregates.

U.S. Pat. No. 4,001,401 discloses the incremental chemical crosslinking of solution-phase hemoglobin, yielding "polyhemoglobin" as soluble nanosized particles (said "polyhemoglobin" term might be regarded as a misnomer, as not more than 13 protein associations were formed per cluster). Similar examples as well as multi-protein hemoglobin associations may be found, which are under study as potential blood substitutes (F D'Agnillo and TMS Chang (1998) "Polyhemoglobin-superoxide dismutase-catalase as a blood substitute with antioxidant properties" Nature Biotechnology 16, 667-671; and Robert Winslow (2006) Blood Substitutes, Chp. 38, Elsevier, London, GB).

US Pat. Appl. 2008/0296231A1 discloses the use of chemical crosslinking to desolubilize micron-sized protein particles after the completion of protein association.

J Lee et al. disclose the formation of chemically crosslinked enzyme aggregates within the pores of inorganic support media ("Simple Synthesis of Hierarchically Ordered Mesocellular Mesoporous Silica Materials Hosting Crosslinked Enzyme Aggregates" Small 1, 744-753, 2005). Here, the pore sizes determined the aggregate size.

US Pat. Appl. 2009/0004278 discloses the preparation of enzymatically crosslinked protein nanoparticles, which were obtained using a bottom-up approach.

B L Simons et al. disclose a dehydrothermal method used to form covalently crosslinked protein lyophilisates ("Covalent cross-linking of proteins without chemical reagents" Protein Science 11, 1558-1564, 2002).

R W Martin and K W Zilm prepared protein nanocrystals (i.e., non-crosslinked) using a bottom-up approach that relied on a rapid batch crystallization technique ("Preparation of protein nanocrystals and their characterization by solid state NMR" Journal of Magnetic Resonance 165, 162-174, 2003).

J C Falkner et al. prepared crosslinked protein nanocrystals using a bottom-up approach followed by chemical crosslinking with glutaraldehyde ("Generation of size-controlled, submicrometer protein crystals" Chem. Mater. 17, 2679-2686, 2005).

As implied from the above, the products of the prior art differ from the product of the invention. In particular, all of the prior art nanoscale protein materials are definable as products of clustering and crosslinking of individual proteins. In marked contrast, the crosslinked protein nanoparticles provided by the invention are definable as nanofragments or nanofragmentation products of crosslinked protein materials (i.e., the precursor materials). The method described in this invention contrasts against the above prior art in that each of the prior art examples invoke a bottom-up and custom-tailored approach to form specific crosslinked nanoaggregates (amorphous nanoclusters) or noncrosslinked nanocrystals, whereas the invention employs a general size reduction technique to reduce the size of any precursor material (again, defined herein as a micron or higher-sized crosslinked protein aggregate or crystal) to the nanoscale. As such, novel crosslinked protein products have been obtained in the invention via a radically different and conceptually opposed approach.

A major novelty of the invention is the size reduction step, which serves to transform large precursor materials into nanosized crosslinked particles. Novel precursor materials of the crosslinked protein nanoparticles of the invention may be obtained via any conventional method used to prepare crosslinked micron-or-greater sized protein crystals or crosslinked protein aggregates as specified in the literature. Alternatively, suitable precursor materials may be purchased. CLEC® of Vertex Pharmaceuticals Inc. and CLEC of Althus Biologicals, Inc. Cambridge, Mass., have commercialized crosslinked micron-sized crystals of thermolysin, elastase, esterase, lipase, lysozyme, asparaginase, urease, nitrilase, hydantoinase, and protease; similarly, CLEA Technologies BV of Delft, NL, has commercialized the sale of desolubilized proteases and lipases as crosslinked aggregates.

The methodology of the invention is notably distinguishable from the prior art, and yields crosslinked protein nanoparticles with markedly different physico-chemical and performance traits. Many nanoparticle characteristics of the invention, such as the extent of deactivation upon crosslinking, are easily predictable based on the precursor materials; said crosslinked protein nanoparticles are generally long-lived under operational conditions and their storage is trivial as dry powder. Their precursor materials also have an extended shelf-life. No such advantage exists for precursors of the prior art, as the prior art provides for products by way of a bottom-up approach, beginning with individual proteins. In the prior art, the technique of protein precipitation has not been used to yield macroscale aggregates prior to crosslinking. Rather, individual solute protein molecules within a solvent environment are linked, forming nanosized protein associations, which are either retained in suspension or are easily dispersable in light of their minute size. Hence, substantial protein precipitation, which precedes crosslinking in the history of the precursor material, defines a delineating step with respect to the prior art, as well as a final embodiment of the current invention.

Properly conducted, the act of crashing out a protein from solution is known by those knowledgeable in the field to have the effect of subtly altering the protein structure, the final aggregate organization, and the inter-protein spaces. Hence, the act of crosslinking individual proteins (or at best nanoclusters) juxtaposed in solution cannot be equated with the dynamics of crosslinking an already-precipitated large aggregate. The latter example, which is used to form the precursor material of the invention, follows entirely different crosslink kinetics, crosslink distributions and spatial dependencies, and displays an intrinsically different product composition upon completion of reaction. The two crosslinking methods are also conceptually distinct on the basis that one describes a homogenous-phase process (i.e., the prior art), whereas the other is truly a heterogeneous-phase process (i.e., the invention). The composition of the proteins and crosslinkers, the density of protein-protein packing, the density and spatial distribution of crosslinking (i.e., collectively quantifiable as spatially density-graded crosslinking inhomogeneities), the chemical nature of crosslinking (chemical, enzymatic, or dehydro-thermal), and the exact site(s) of crosslinking per protein, will differ between invention and prior art. Such will be the case, even if the same base protein comprises each material; the final chemical composition of the particles, the inter-protein connectivities within the particles, and the relative spatial orientations of the proteins will differ. As such, the characteristics of the crosslinked protein nanoparticles described by the invention differ from the nanosized crosslinked protein materials described in the prior art. Hence, the crosslinked nanoaggregates arising from the bottom-up and top-down strategies actually define two distinct and distinguishable product classes. In the case of the crosslinked protein nanocrystal products of the invention, the spatially density-graded crosslinking inhomogeneities, the particle shapes as well as their surface topologies and energies (arising due to nanonization), the material stresses (which alter material properties), and possibly the polymorphism (a trait of the crystallization procedure) will differ compared to the nanosized crosslinked protein materials described in the prior art.

With respect to micron-sized crosslinked protein aggregates and crystals, the invention offers the clear benefits of improved biological activity (due to the high surface, which permits better interaction and, where applicable, mass transfer) and excellent bioavailability (nanoparticles are known to be absorbed and internalized into the body by various routes). Indeed, the characteristics of the crosslinked protein nanoparticles of the invention distinctly differ from their precursor materials.

In view of the above two paragraphs, the invention provides for new crosslinked protein nanoparticle products, which display a set of advantageous traits. Said nanoparticles are the nanofragment products of crosslinked micron-or-greater sized protein aggregates or crystals.

DETAILED DESCRIPTION OF SPECIFIC EMBODIMENTS

The novelty of the present invention relates to the reduction of the physical size of micron-or-greater-sized crosslinked protein materials and the fact that said nanonization (i.e., size reduction to the nanoscale) method enables the preparation of new crosslinked protein nanoparticle products.

Crosslinked protein crystals (micron-sized) are especially renowned for their performance stability compared to solution phase proteins and noncrosslinked protein crystals. The improved robustness upon crosslinking has also been expressed in the case of micron-or-greater sized crosslinked protein aggregates (i.e., crosslinked protein precipitates and lyophilisates). Said crosslinked protein products are even biologically active in organic solvents and at temperatures nearing 100° C. In light of the observed "toughening" effect following crosslinking, it was particularly surprising to note that crosslinked protein aggregates were easier to nanonize than the corresponding uncrosslinked material. Assessed more systematically, it was found that the act of covalently crosslinking protein aggregates and crystals directly facilitated the size reduction process. Not only were smaller particles formed with the crosslinked material, but these particles were also formed in a shorter period under the application of identical forces and fragmentation conditions. Even manual grinding (i.e., by hand) yielded crosslinked protein nanoparticles easily, when a precursor material as described by the invention was used.

The nanonization event comprises the application of mechanical or hydrodynamic shear, crushing mechanical forces, and/or sonic or hydrodynamic cavitation, the application of low temperatures to reduce material plasticity and chemical degradation, the addition of scavenger molecules to reduce chemical degradation, the addition of solids to aid size reduction (if advantageous), and the addition of stabilizer molecules to prevent/limit re-agglomeration following fragmentation. By applying physical stresses to the precursor material, macroscopic-sized crosslinked protein particles are fragmented, yielding a distribution of particles of sub-micron size, ideally lying within the 50-200 nm range. Chemicals present in the nanonization media may be adjusted on a case-to-case basis to facilitate controlled particle fragmentation, to prevent re-association of nanonized particles, and to retain the biological integrity of individual protein components comprising each particle. The product obtained using the described method will display biological activity, enhanced bioavailability and superb mass-transport traits. Optionally, these crosslinked nanosized protein products may be assorted into more specific size ranges by using various physical methods. As well, they may be surface-functionalized in subsequent undertakings.

As stated before, the size reduction process is fine-tunable by means of adjusting the processing options. The use of additional chemicals in the nanonization medium, particularly grindable but chemically inert solids, can promote controlled particle fragmentation. In cases, such as the dry grinding of crosslinked protein powders, these additional solids should be physically harder than the crosslinked proteins. Ideally, they should be hard enough to facilitate nanonization of the crosslinked protein but not excessively hard to damage the protein component or to slow the nanonization process. The addition of inert solids is particularly helpful when very small amounts of protein are to be ground; in such case, said solids take on a triple role, adding extra material to the system (assuming a carrier role), aiding the grinding process, and stabilizing the nanoparticles formed. Cooling in liquid nitrogen, followed by manual grinding of protein and said powdered grinding additives (in an agate mortar), can also yield nanoparticles. Said protocol is particularly well-suited for easily damaged proteins. Interestingly, cooling is not necessarily required, as manual grinding at room temperature also yields nanoparticles within a remarkably short period. In cases, such as the "wet" grinding of crosslinked protein particles (e.g., mechanical homogenization of particles suspended in aqueous-phase or organic-phase media), stabilizers should be used to limit re-aggregation. These agents should be present during and following the hydrodynamic shear-induced grinding process, thereby optimizing the fraction recovered as nanoparticles. Cavitation methods can also facilitate the wet "grinding" (i.e., size reduction) of said precursor materials, given enough power density. Radical scavengers are particularly recommended under said conditions, as cavitation can generate reactive chemical species from solvent molecules. Hydrodynamic cavitation is particularly attractive, as a technique, to achieve fragmentation of micron-sized crosslinked particles in a continuous flow process.

From a bioavailability viewpoint, said products of the invention are advantageous over non-coated uncrosslinked protein particles, crosslinked micron-or-greater sized protein particles, and individual proteins. Firstly, the crosslinked protein nanoparticles can be absorbed by the intestine and GALT system, whereas crosslinked micron-sized particles are too large. Secondly, stomach acid will not significantly damage the crosslinked nanoparticles, whereas re-solubilized individual proteins cannot survive the journey to the small intestine. A specific crosslinked enzyme nanocrystal, produced by said method, is depicted in FIG. 1, as a therapy to restore the metabolic balance of a lysosomal storage disorder, as per the mechanism known to those familiar with enzyme replacement strategies. That being said, the potential applications of embodiments of the present invention are not limited to medicine.

There are many other advantages of the current invention. The ability to grind the precursor material permits the fine-tuning of particle sizes. The size reduction process has so many fewer variables compared to the bottom-up approach that a well-developed system can easily yield nanoparticles with reproducible size distributions. The same utility is not readily available to bottom-up approaches. Bottom-up processes in solution generally experience intrinsic limitations in controlling the particle size. Like many solute molecules, non-crosslinked proteins that serendipitously form nanoclusters in solution may tend to assemble further, yielding high molecular weight, micron-scale complexes. The use of stabilizers has met with some success in maintaining the nanosize of newly formed protein associations. Conversely, in situ chemical crosslinkers have been used to prompt the direct solution-phase assembly of sluggishly assembling protein molecules; unfortunately, these agents also promote the formation of very high molecular weight complexes, even in the presence of stabilizers. It is similarly challenging to prepare crosslinked protein nanoparticles in cases where the chemical crosslinkers are introduced only after formation of the protein nanoparticles; as implied previously, the inherent tendency for nanoscale protein complexes to associate further (or to re-dissolve) can alter the particle sizes in the time elapsed prior to commencing this second manipulation. Finally, inter-particle crosslinking is always a risk to consider when working with chemical crosslinkers; in many instances, inter-particle crosslinking competes with intra-particle crosslinking (i.e., inter-protein and intra-protein crosslinking within one particle), yielding uncontrollable size increases, which overpass the nanoscale and yield crosslinked micro-scale particles.

As discussed previously, the crosslinking process in the history of the precursor material bestows the surprising and strikingly effective trait of easy grindability, proving advantageous over noncrosslinked protein materials. It seems that crosslinking yields less compliant protein particles. The fact that the particles are less compliant permits fragmentation to continue effectively at smaller length scales. With crystalline proteins, which are highly solvated, crosslinking helps to preserve crystallinity upon fragmentation. Crosslinking also preserves the structural stability of protein units comprising the nanoparticles, hence promoting the retention of bioactivity during the fragmentation step.

Crosslinked protein nanocrystals have not been prepared industrially, but one publication exists in the prior art using a bottom-up approach. Similarly, crosslinked nanosized protein associations such as nanoaggregates have been prepared, for very specific applications, using only a bottom-up assembly approach. The embodiments of the present invention address this dearth of available crosslinked nanoparticles as well as their production technology. In particular, embodiments of the present invention expand on the size reduction principle and specifically describe the preparation of crosslinked protein nanoparticles using physical means, which are based on the application of stresses that lead to fragmentation. With readily prepared starting materials, the size reduction approach of this invention is general, industrially adoptable, easily scalable, and conveniently controllable. Hence, large amounts of crosslinked protein nanoparticles can be prepared controllably and conveniently by means of this invention.

When comparing the performance of crosslinked, micron-sized protein materials against the corresponding individual proteins in solution, the former prove longer-lived, easily recoverable, more hydrolytically and proteinase stable, and more tolerant to temperature, organic solvent, and pH extremes. The crosslinked protein nanoparticles of the invention boast similar advantages over individual proteins. These particles also possess specific advantages over established micron-sized particles, such as enhanced mass-transfer, enhanced reactivity, and improved bioavailability and efficacy. Having observed that the nanosize of these particles will directly affect the performance traits, it is fair to reason that such nanoparticles can replace the role of many individual proteins, as well as many micron-sized crosslinked protein particles. An examination of the examples section presented herein will show an observable improvement of bioactivity upon size reduction.

Figure 1:
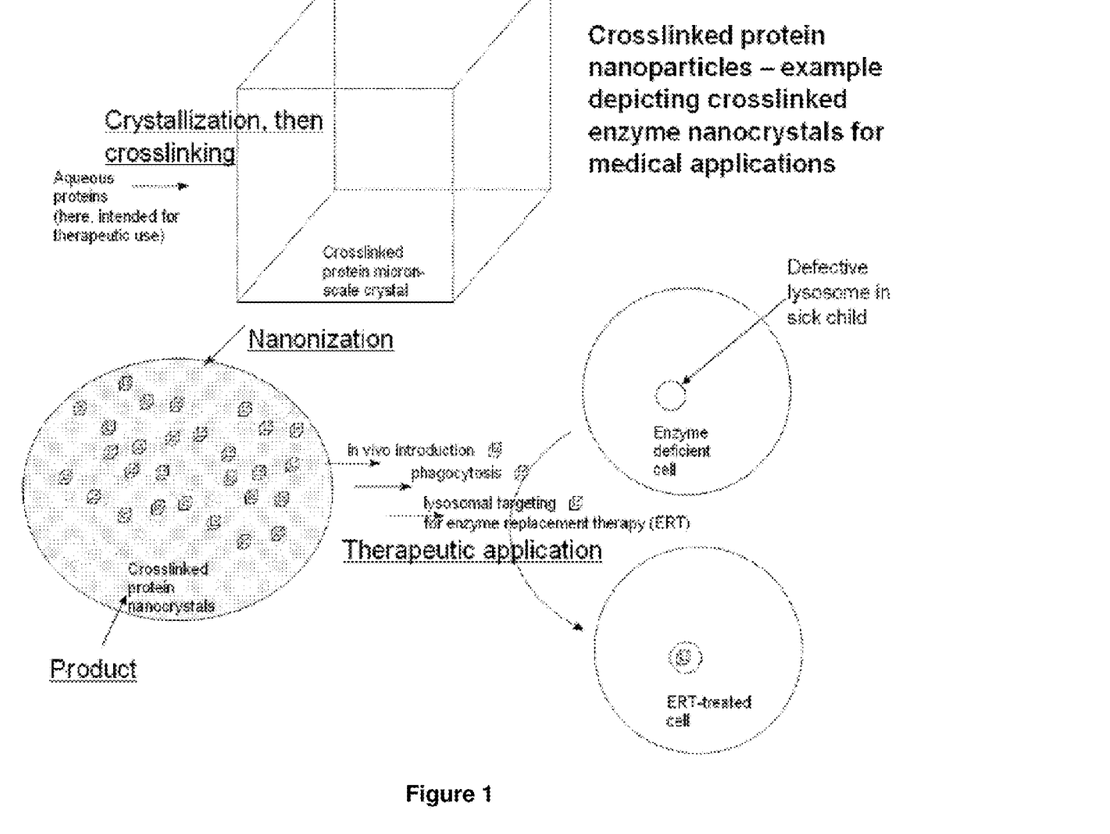
FIG. 1 illustrates the use of crosslinked protein nanoparticles (nanocrystals in the depiction) for treatment/symptom management of lysosomal storage disorders.

Most importantly, the nanosize of these particles may prove very useful in therapeutic applications such as enzyme replacement therapy. The rationale of this claim rests on literature findings based on other nanoparticles, which strongly suggest that enzyme nanoparticles, appropriately treated, will retain their biological activity and experience multiple uptake routes, good systemic bioavailability, improved brain entry, rapid cellular internalization, targeted delivery to lysosomes and greatly improved in vivo stability in comparison to monomeric enzymes or soluble enzyme derivatives. As lysosomal storage disorders underscore an enzyme deficiency within the organelle, the present invention could restore homeostasis and serve as an improved and more general alternative to established drug delivery strategies. The rationale of this therapy is illustrated in FIG. 1.

Embodiments of the present invention are amenable to many forms of enzyme therapy. Enzyme deficiencies could be directly compensated, as in the case of established replacement therapies, or enzyme deficiencies could be trivialized by blocking the supply route of additional substrates, as in the case of substrate reduction/inhibition therapies. The basis to extend therapies beyond the scope of lysosomal storage disorders is justifiable, as crosslinked nanoparticles can resist the action of acidic proteolysis as well as other hydrolytic processes present in the cytosol and intercellular fluids. The small size of said nanoparticles implies easy injectability, good absorption via sublingual, buccal and GALT (gut-associated lymphoid tissue) mucosal processes, and unrestricted access to flow-constricted regions such as diseased blood vessels and traumatized interstitial spaces. It follows to reason that crosslinked protein nanoparticles could display merit in treating many orphan diseases like lysosomal storage disorders and cystic fibrosis. As well, it may serve to aid digestive ailments, enzyme-responsive cancers, diabetic and hypoxic conditions, reperfusion-related injuries, and chronic wounds. With due consideration to the inherent potential advantages listed above, many key therapies could follow this approach, particularly protein-based drugs that target the brain.

Product Details:

The current invention provides for a covalently crosslinked protein nanoparticle, sized 10-999 nm and preferably 50-200 nm, suitable for enabling biotechnology, cosmetic, pharmaceutical and biomedical applications, characterized in that said nanoparticle, which comprises of one or more types of protein, adsorbates, and at least one type of zero-or-greater length inter-protein crosslink, is obtained as the nanofragmentation product (i.e., it is a nanofragmentation product) of a compositionally equivalent or near-equivalent precursor material, having a physical length, in each dimensional axis, of at least one micron. The term "near equivalent" is used to allow for minor changes that may occur during size reduction, for example solvent exchange, solvent displacement or altered inter-protein packing. The term "nanofragmentation" is used to convey the idea that the micron-or-greater sized precursor material of the invention is fragmented or subdivided into nanosized fragments (hence coining the term nanofragmentation). The protein component may comprise of one or more of the enzyme, hormone, receptor, structural, transport or antibody classes of proteins. More specifically, the protein component may consist of hydrolase, prohydrolase, isomerase, transferase, oxidoreductase, lyase, ligase, insulin, glucagon, glucagon-like peptide, extendin, extendin derivatives, symlin, somatokine, insulin antibody, proinsulin antibody, interferon, anticancer monoclonal antibodies, anticancer vaccines, natrecor, antiplatelet agents, cytokines, tumour necrosis factor alpha, interleukin 1 receptor antagonist, HIV-1 inhibitory peptide T20, artificial protein 5H-ex, somatostatin, HIV fusion inhibitor T-1249, antimicrobial proteins, lysozyme, lactoferrin, bacteriocin, interleukin-2, angiotensinogen, angiotensin, angiotensin converting enzyme inhibitor, gelatin, collagen, procollagen, chitosan, silk protein, keratins, myosin, actin, growth hormone, albumin, globulin, hemoglobin, myoglobin, and/or cytochromes. Looking to the method of preparation, it is clear that upon size reduction, each crosslinked protein nanoparticle will reflect the chemical composition and crosslinking history of its precursor material. The precursor is a micron-or-greater sized protein aggregate (coming from either a protein precipitation event or lyophilization event) or a protein crystal, which is subsequently crosslinked. The nature of the crosslinking of the precursor can be chemical, enzymatic or dehydrothermal, and in every case, it is covalent. The crosslinks may vary from zero-length, as in the case of directly-joined proteins treated with carbodimide or heat under vacuum (i.e., dehydrothermally), to 20-or-greater carbon-unit inter-protein crosslinks using bi-, tri- or polymeric linkers. The chemical agent, which forms, or prompts crosslink formation in the precursor material, may be soluble or dispersible in water or organic solvent. The chemical agent is not limited to and can be any one of carbodiidmide, dextran aldehyde, dialkyl diimidates and other bifunctional or trifunctional crosslinkers possessing up to 20 bridging carbon atoms, and/or glutaraldehyde polymer, starch aldehyde, polyamines, organosilicones and other polymeric linkers with at least 5 functional groups. In the case of enzymatically formed crosslinks, the precursor may have been treated with any suitable hydrolase, transferase and/or oxidoreductase, and possible a transaminase such as transglutaminase. In the case of dehydrothermally formed crosslinks, the precursor material may have been heated at 70-120° C. for 6-48 h under vacuum conditions. The crosslinked protein nanoparticle and precursor, being largely protein-based, will be expected nonetheless to harbor adsorbates along the surface. The nature of the adsorbate shall reflect the preparation history of the precursor materials and the processing history leading to the nanoparticle. The nanoparticle and precursor will bear adsorbates, which may comprise of one or many of water, organic solvent, salt, lyoprotectant, cryoprotectant, and/or surfactant.

Method Details.

The invention discloses a method to prepare a crosslinked protein nanoparticle. The steps comprise of preparing micron-or-greater sized protein aggregates or crystals, and crosslinking the aggregates or crystals to yield a precursor material. The precursor is then subjected to a size reduction process, which achieves nanonization, yielding a crosslinked protein nanoparticle. The size reduction process invokes the application of mechanical shear forces along the precursor material. For instance, the necessary mechanical shear forces may be generated using a conventional high-shear mixer/compounding device operated at 100-15000 rpm and preferably from 1000-6000 rpm, with application times ranging from 30 s-10 min at temperatures below 120° C. The size reduction process may also invoke the application of hydrodynamic shear stresses, wherein said hydrodynamic shear stresses are applied to the precursor material in an aqueous or organic medium using, for instance, a homogenizer as dispersing/mixing instrument. In the case of homogenization, the prescribed operating conditions are 100-500 rpm and preferably 1000-2000 rpm, 5 min-3 h and preferably 30 min-1.5 h, and temperatures below 100° C. Ironically, instruments are not necessarily needed, as manual grinding (crushing mechanical forces) in the presence of excess potassium iodide using a mortar and pestle also yields crosslinked protein nanoparticles by way of this invention. The precursor/powder (i.e., grinding aid) weight ratio can range anywhere from 2:1 to 1:1000 by weight. Finally, nanonization can also be achieved using pressure gradient stresses, which are generated via sonic or hydrodynamic cavitation at temperatures below 80° C. A further aspect of the size reduction method is the optional use of cooling, before and during the grinding process, which can embrittle the precursor material as well as reduce unwanted decomposition. A convenient source of cooling is liquid nitrogen. A further aspect of the size reduction method is the option to include scavenger molecules, where deemed appropriate, in order to reduce protein decomposition arising from radical processes, heterolytic bond fission processes and oxidation processes. Incorporating such a precaution can prove useful in the case of cavitation processes, which are known to generate substantial free radicals. A useful amount of scavenging agent to add is 0.01-2% by weight with respect to the precursor material. Said scavengers are not necessarily limited to and can incorporate one or more of alpha-tocopherol, naringenin, retinol, iodide, coenzyme Q10, melatonin, carotenoid terpenoids, flavonoid polyphenolics, phenolic acids and esters, glutathione, N-acetylcycleine, phytic acid, oxalic acid, citric acid, eugenol, xanthones, curcumin, flavonolignans, R-lipoic acid, uric acid, carotene, ubiquinol, ascorbic acid, butylated hydroxytoluene, bisulfite, and/or thiosulfate. Solid powder additives are also recommended to facilitate the process of physical size reduction. The precursor and solid powder can be combined prior to size reduction in a weight ratio ranging from 2:1 to 1:1000, respectively. The choice of solid powder may comprise of potassium iodide, sodium iodide, sodium chloride, other alkali salts, alkaline earth salts, active carbon, silicon dioxide, aluminum oxide, titanium dioxide, chitin, keratin, and/or polyimide. A further aspect of the size reduction process is the addition of stabilizer molecules in a 2-to-100 fold weight excess in order to prevent/restrict re-agglomeration. The choice of stabilizer molecule is not necessarily limited to and can be one or more agents among potassium iodide, sodium iodide, sodium chloride, or any alkali or alkaline earth salt, ammonium salts, carbohydrates, polyols, polyvinylpyridine, polyvinylpyrolidone, polyamides, citric acid, ascorbic acid, albumin, hypromellose and/or gelatin.

Application.

The crosslinked protein nanoparticle, produced by the method of the invention, will improve the performance of protein-based therapies through improving biological activity and bioavailability. Most any administrative route stands to benefit from this invention, including oral, buccal, sublingual, GALT, intraperitoneal, intramuscular, subdermal, subcutaneous, intrathecal, intraparenchymal, and IV. A particular target of this invention is the restoration of the metabolic imbalance arising from lysosomal storage disorders. The fact that nanoparticles are internalized into cells, and the fact that foreign materials are directed into lysosomes, serves to suggest an effective therapy for said defective organelle. The fact that crosslinking prevents rapid proteolysis will serve to promote oral drug delivery (a definite plus for small children) of said crosslinked protein nanoparticles. The proteolytic resistance of said nanoparticles will also permit long in vivo activity in the lysosome, or other regions inflicted with a pathological condition.

EXAMPLES

Example 1

Nanonization of Alcalase CLEA
(CLEA=Crosslinked Enzyme Aggregates)

Figure 2:
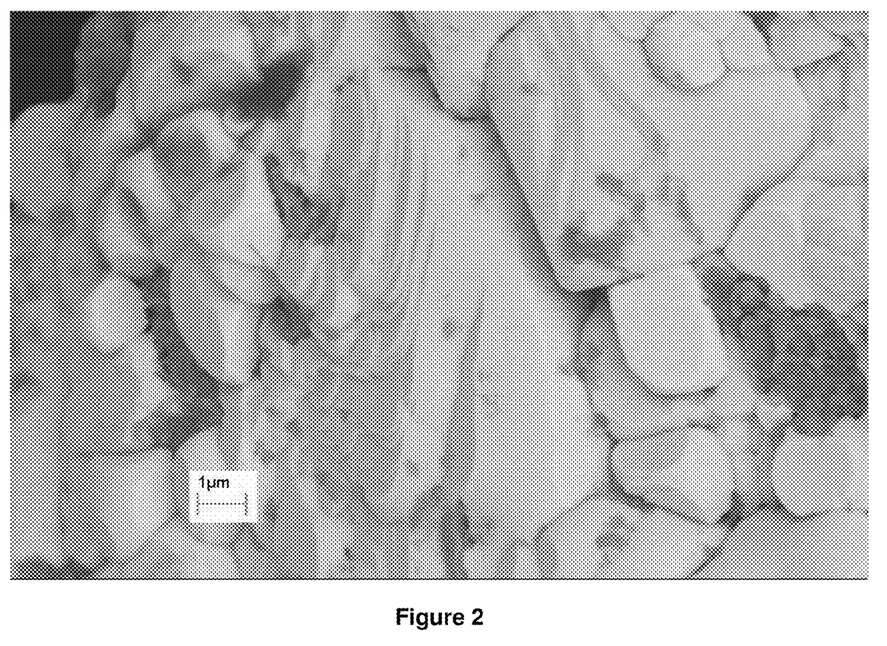
FIG. 2 shows the image of Alcalase crosslinked enzyme nanoaggregates and re-aggregations of said nanoparticles together with potassium iodide particles (dark nanoparticles and re-aggregations on a white potassium iodide background). Said image was taken using a SEM configured in backscattering mode (5 kV). The precursor (Alcalase CLEA) was nanonized in the dry state using mechanical shear in the presence of potassium iodide.

Alcalase CLEA (1 g, CLEA Technologies BV) was gently mixed with potassium iodide (69 g) as grinding aid and stabilizer. The mixture was ground under mechanical shear using a G series GELIMAT G1 mixer/compounder obtained from Draiswerke, Inc., Mahwah, N.J. To being, the material was introduced into the chamber through a top hopper with a locking slide. This machine has a horizontally extending cylindrical chamber with a central shaft provided with staggered generally radially extending mixing elements. The chamber is equipped with an ammeter shaft drive measuring energy input or power dissipation and a temperature sensor. The shaft was rotated (5000 rpm, 5 min) while never allowing the sample temperature to exceed 63° C. Once completed, the finely-ground mixture was discharged rapidly from the chamber under the action of centrifugal force. SEM microscopic analysis (FIG. 2) using a LEO Supra 35 VP instrument configured in the backscattered electron mode (5 kV) illustrated nanoparticles of Alcalase (dark particles on a white potassium iodide background) as well as re-aggregated nanoparticles (refer to the DLS results section). Said mixture was found to retain biological activity. Nanoparticles were not observed in the unprocessed precursor material (image not shown).

Example 2

Nanonization of Savinase CLEA

Figure 3:
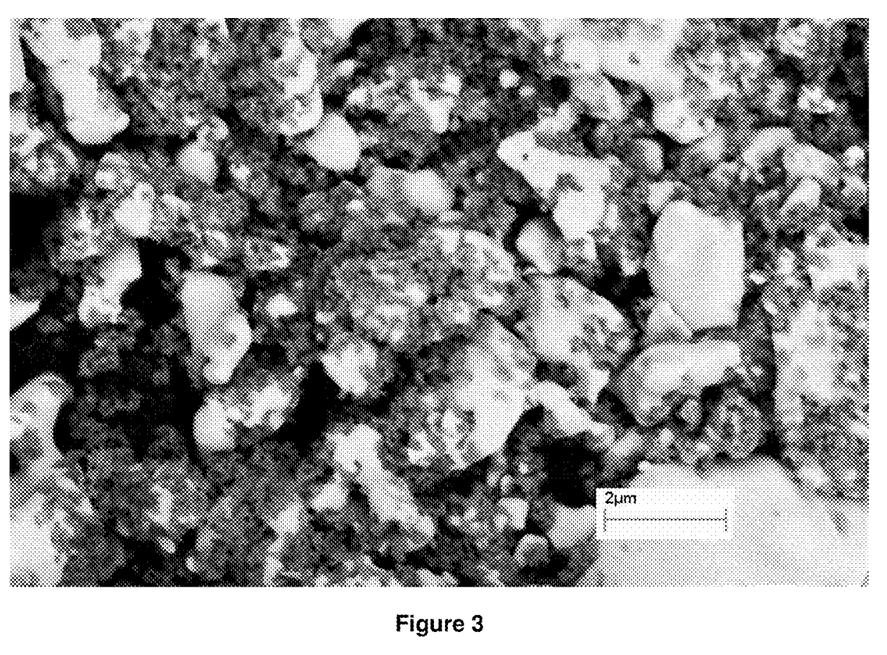
FIG. 3 shows the image of Savinase crosslinked enzyme nanoaggregates and re-aggregations of said nanoparticles together with potassium iodide crystals, which served previously as stabilizer during wet nanonization. Said image, taken using a SEM configured in the backscattered electron mode (4 kV), illustrates nanoparticles of Savinase (dark nanoparticles on a white potassium iodide background) as well as re-aggregated nanoparticles (refer to DLS results section). The precursor (Savinase CLEA) was nanonized using a homogenizer device while suspended in an aqueous potassium iodide solution.

Savinase CLEA (10 mg, CLEA Technologies BV) was placed into a 50 ml Falcon tube and suspended in distilled water (10 ml) containing predissolved potassium iodide (200 mg) as stabilizer. Hydrodynamic shear was applied to the suspension (1500 rpm, 1.5 h, 30-35° C.) using a 1600 W PT-MR 6100 Polytron Homogenizer (Dispersing and Mixing Technology by Kinematica) fitted with a PT-DA 6050/2TM dispersion probe. A sample was extracted, flash frozen in liquid nitrogen, and lyophilized. SEM microscopic analysis of the sample (FIG. 3) using a LEO Supra 35 VP instrument configured in the backscattered electron mode (4 kV) illustrated nanoparticles of Savinase (dark particles on a white potassium iodide background) as well as re-aggregated nanoparticles (refer to DLS results section). Said mixture displayed 340% biological activity with respect to the untreated savinase from the stock bottle. Nanoparticles were not observed in the unprocessed precursor material (image not shown).

Example 3

Nanonization of Savinase CLEA

Figure 4:
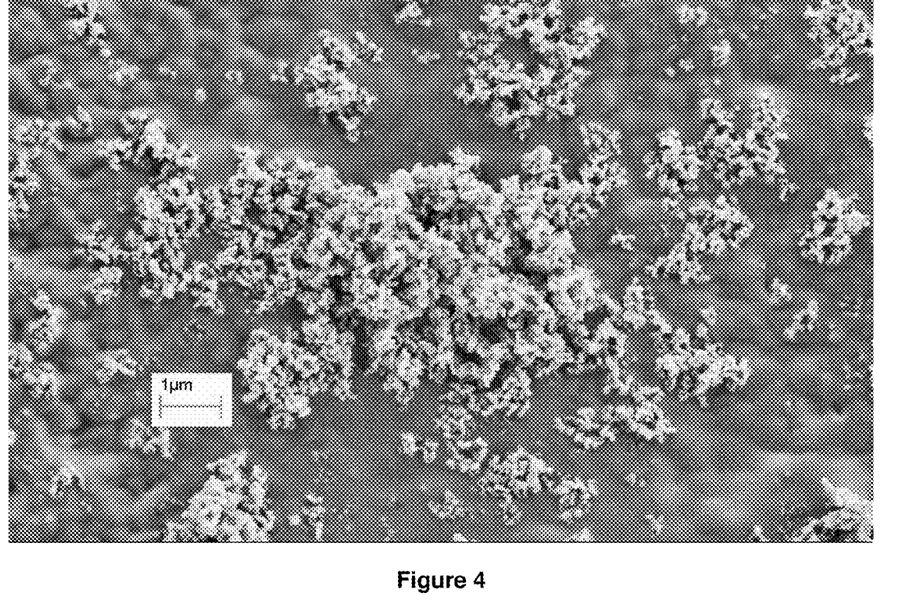
FIG. 4 shows the image of Savinase nanoaggregates and substantial re-aggregations of said nanoparticles. Said image, taken using a SEM configured in the secondary electron mode (2 kV), reveals nanoparticles and re-aggregations against a carbon-backed background. The precursor (Savinase CLEA) was nanonized using a homogenizer device while suspended in water. No stabilizer had been added.

The procedure of example 2 was repeated except no potassium iodide was added as stabilizer and the SEM analysis was conducted in secondary electron mode (2 kV) against a carbon-backed background. Fewer free nanoparticles were obtained. In fact, most of the product was comprised of micron-sized re-aggregated nanoparticles (FIG. 4). Interestingly, even these aggregates appeared to be weakly associated, as implied by the DLS results (see DLS section). Moreover, an impressive biological activity of 590% was noted with respect to the untreated micron-sized precursor (SEM not shown), attesting to the survival and advantageous features of said nanoparticles.

Example 4

Nanonization of Savinase CLEA

Figure 5:
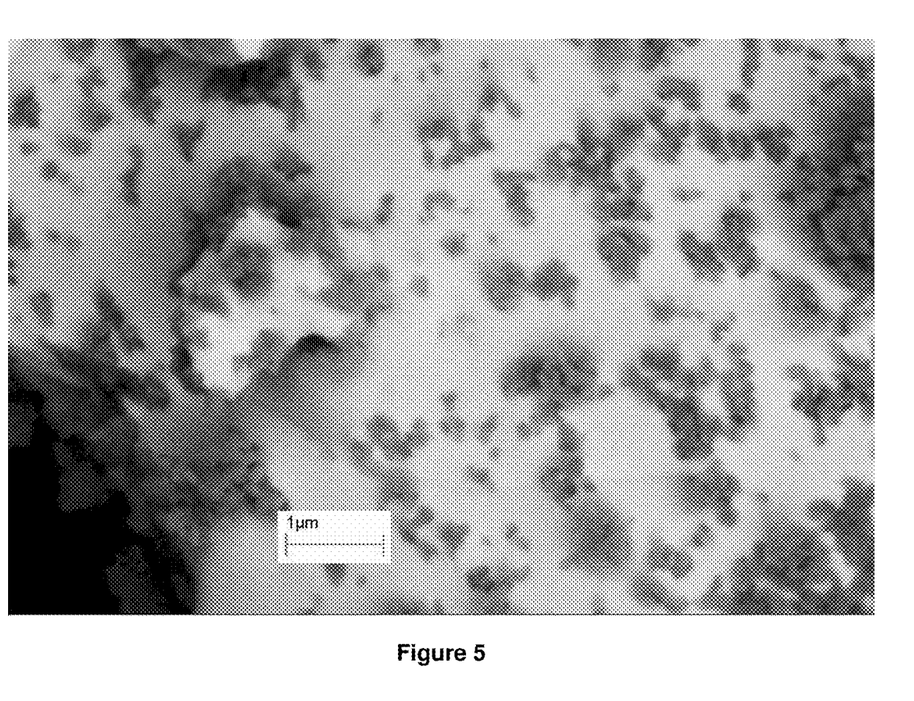
FIG. 5 shows the image of Savinase nanoaggregates and few re-aggregations of said nanoparticles together with potassium iodide particles. Said image, taken using a SEM configured in backscattered electron mode (4 kV), reveals a very effectively nanonized material. The precursor was ground by hand in a mortar without protection from humidity. Mechanical crushing was achieved in the presence of potassium iodide as grinding aid, carrier, and nanoparticle stabilizer. The precursor material was Savinase CLEA.
Figure 6:
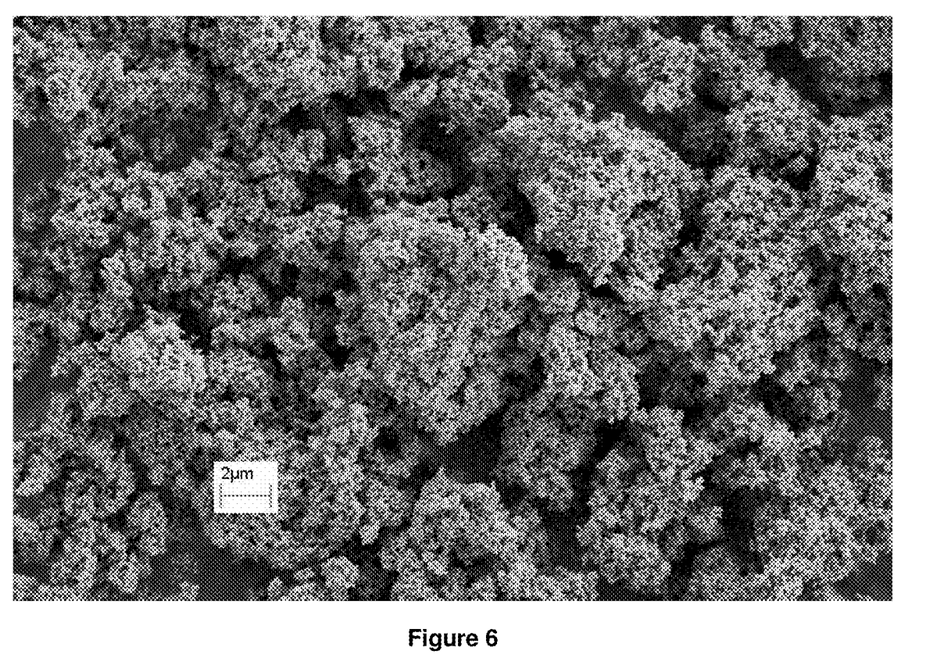
FIG. 6 shows images of Savinase CLEA (non-nanonized control) taken using a SEM configured in secondary electron mode against a carbon background at 2 kV.

Savinase CLEA (20 mg, CLEA Technologies BV) was ground by hand (20 min, RT) in an agate mortar without protection from humidity. Potassium iodide (400 mg) was used as grinding aid and stabilizer. The crushing mechanical action was discontinued once heterogeneous regions could no longer be seen by eye. SEM microscopic analysis (FIG. 5) using backscattered electrons (4 kV) illustrated nanoparticles of Savinase (dark particles on a white potassium iodide background). Very few re-aggregated nanoparticles (refer to the DLS results section for further discussion) were noted, attesting to the potential utility of manual grinding methods. A biological activity of 265% was quantified with respect to the untreated CLEA stock (shown in FIG. 6, using the secondary electron mode against a carbon background at 2 kV).

Example 5

Nanonization of Crosslinked Hemoglobin Aggregates

Figure 7:
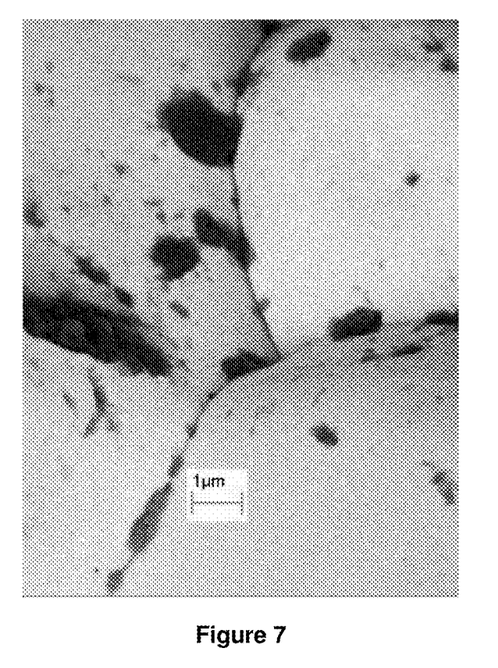
FIG. 7 shows the image of crosslinked hemoglobin nanoaggregates and potentially one or both possibilities comprising of re-aggregated nanoparticles of said material or micronsized crosslinked hemoglobin aggregates (signifying incomplete nanonization). The image was obtained using a SEM configured in the backscattered electron mode (5 kV). The precursor material was prepared in-house as specified in the examples section.

All crosslinking and workup steps were achieved at 4° C. Bovine hemoglobin (Sigma) was crosslinked with glutaraldehyde. The solution (5 ml, 100 mg Hb/ml) was dumped into ammonium sulfate solution (45 ml, 3M) and left static (1 h) to yield insoluble aggregates. A fresh glutaraldehyde solution (1 ml, 25%) was added to the reaction vessel, vortexing was applied (3 s), and the mixture was incubated under mild shaking (20 h). Tris(hydroxymethyl)aminomethane (TRIS) buffer (2 ml, 2M, pH 8) was added thereafter and the reaction was gently incubated (2 h) on a mechanical shaker. The protein sample was recovered via centrifugation (10 min, 7000 rpm), thrice washed with 0.1M TRIS buffer (pH 8) and once with water (washings depict 15-20 min agitations; after completion of each washing, the sample was spun down for 10 min at 7000 rpm). The crosslinked hemoglobin aggregate product was dried under vacuum conditions (RT). Protein (0.5 g) was sifted together with potassium iodide (69 g). The mixture was ground under mechanical shear using the Gelimat compounder as described in example 1. SEM analysis (FIG. 7. backscattered electron mode, 5 kV) illustrated the presence of nanoparticles (black particles on a white potassium iodide background), and either micron-sized particles or nanosized aggregates. The control and mechanically processed crosslinked hemoglobin samples were biologically active, the latter being slightly more.

Protease Bioassays.

The size-reduced Savinase and Alcalase CLEAs were assayed (2 h, 37° C., 550 rpm) using gelatin (1 wt % in phosphate buffered saline (PBS) buffer) as substrate. Desalting prior to the assay was not attempted. The protein to be assayed was reconstituted in water to give a final concentration of 1 mg/ml. Equal volumes of protein suspension and gelatin-PBS solution were combined to begin the assay. Non-processed CLEAs were similarly assayed. Zero-protein controls consisted of water (example 3) or an appropriately prepared potassium iodide solution (the remaining examples). The assay medium was later centrifuged (12000 rpm) in an Eppendorf microcentrifuge to remove any insoluble materials, and the supernatant was analyzed by delivering i-propanolic ninhydrin solution (1 wt %) thereon to give a 2:1 aqueous/organic ratio by volume (45 min, 70° C.). Following color development, the reaction was cooled and quantified spectrophotometrically at 570 nm. Dilutions were made prior to measurement using isopropyl alcohol in cases where Beer's Law was exceeded (i.e., A>1.5). All comparisons were relative and were made against the untreated CLEA stocks. Other bioassays, based on the substrate N-acetylglycine ethyl ester, can be performed at pH 7.5 and 40° C., as per any established method used to assay Subtilisin.

Crosslinked Hemoglobin Aggregate Bioassay.

A modified assay procedure based on K Zhang et al. ("Stopped-flow spectrophotometric determination of $H_2O_2$ with Hb as catalyst" Talanta 51, 179-186, 2000) was implemented using o-phenylenediamine as color development reagent. Sodium phosphate (10 mM, pH 8) was used in place of the prescribed buffer system. Following incubation (1 h, 450 rpm, RT), any particulate material was separated from the reaction solution via centrifugation. The spectrophotometric detection of color was carried out exactly as prescribed in the publication.

Particle Size Analysis of Size-Reduced Precursor Materials (i.e., Taken from Examples 1-5) Using Dynamic Light Scattering (DLS).

Figure 8:
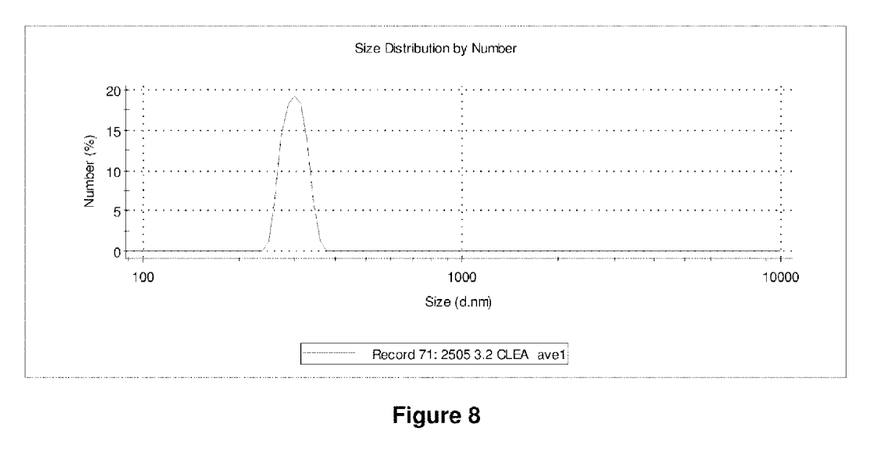
FIG. 8 shows the averaged number size distribution profile of Alcalase CLEA, ground in a Gelimat G-1 instrument with potassium iodide (referring to example 1). Data was collected using a Malvern Instruments Nanoseries Zetasizer instrument (i.e., Nano-ZS brand, configured with a 633 nm laser).
Figure 9:
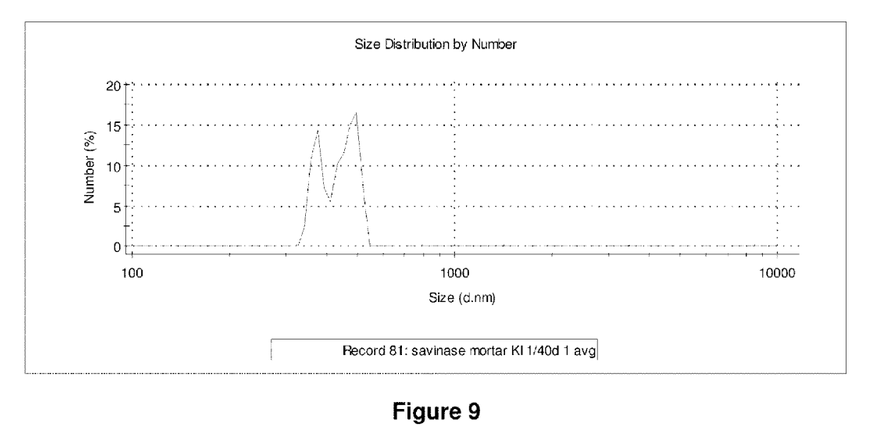
FIG. 9 shows the averaged number size distribution profile of Savinase CLEA, ground by hand in a mortar with potassium iodide (referring to example 4). Again, data was collected using said Malvern Instruments Nanoseries Zetasizer instrument.

The nanoparticle samples (previously flash frozen and lyophilized for storage in the case of examples 2-3) were reconstituted in distilled water. The suspensions afforded were stabilized, as needed, by the addition of more salts. With sample preparation being optimized, the analytes were then transferred into a 300 μl cuvette and placed inside a Malvern Instruments Nanoseries Zetasizer instrument (i.e., Nano-ZS brand, configured with a 633 nm laser). Each sample was read immediately after preparation, as excessive delays generally led to aggregation (typically yielding 1-3 micron particles) and even sedimentation (as evidenced by signal loss after an extended period—particle dissolution, the second cause of signal loss, is not an option in the case of CLEAs). Triplicate analyses were conducted for samples taken from examples 1-5, yielding particle sizes of generally not more than 500 nm (with a reasonable size distribution). Shown explicitly (FIGS. 8 and 9) are the averaged number size distribution spectral profiles, respectively, of two such analyses, namely, Alcalase CLEA, ground in a Gelimat G-1 instrument with potassium iodide (i.e., example 1), and Savinase CLEA, ground by hand in a mortar with potassium iodide (i.e., example 4). For analysis purposes, a particle absorbance reading of 0.3 A (1 mg CLEA/ml) and 0.024 A (0.025 mg CLEA/ml), respectively, was input into the analysis program. Among the examples 1-4, local regions in many of the SEM images appeared to portray micron-sized particles; however, these larger particles were in fact re-aggregated clusters of crosslinked nanoparticles, as evidenced by the DLS results. The DLS results were therefore quite significant to the invention, as they pointed to a nanofragmentation process, which was essentially quantitative, yielding biologically active nano-sized materials. The DLS profile for examples 1-3 was unimodal and for example 4 was bimodal. The DLS profile for example 5 was also bimodal; however, in this example, nanoparticles, and either micron-sized or re-aggregated nanoparticles, were both observed. Overall, the size distribution of the nanoparticles of each SEM micrograph was consistent with the corresponding DLS readings (light scattering profiles generally indicated particles of approximately 40-50% larger diameter).

Throughout the document, example embodiments are given. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments or alternatives of the foregoing description.

I claim:

1. A method to prepare a crosslinked protein nanoparticle by a process comprising the steps of:
preparing micron-or-greater scale protein aggregates or crystals, and
crosslinking the aggregates or crystals to obtain a precursor material, characterized in that said precursor is subjected to a size reduction process that causes nanonization, yielding a final product.

2. A nanonization method according to claim 1, wherein mechanical shear forces are applied to said precursor material.

3. A nanonization method according to claim 1, wherein mechanical shear forces are applied to said precursor material using a conventional high-shear mixer/compounding device operated at 100-15000 rpm.

4. A nanonization method according to claim 1, wherein mechanical shear forces are applied to said precursor material from 30 s-10 min at temperatures below 120° C.

5. A nanonization method according to one of claims 1-2, wherein hydrodynamic shear stresses are applied to said precursor material.

6. A nanonization method according to one of claims 1-2, wherein hydrodynamic shear stresses are applied to said precursor material in aqueous or organic media using a homogenizer as dispersing/mixing instrument operated at 100-5000 rpm.

7. A nanonization method according to one of claims 1-2, wherein hydrodynamic shear stresses are applied to said precursor material from 5 min to 3 h at temperatures below 100° C.

8. A nanonization method according to one of claims 1-3, wherein crushing mechanical forces are applied to said precursor material.

9. A nanonization method according to claim 8, wherein the crushing mechanical forces are applied via manual grinding using a mortar and pestle in order to crush said precursor material, the precursor, and a solid powder as grinding aid, being administered in a respective ratio ranging from 2:1 to 1:1000 by weight.

10. A nanonization method according to one of claims 1-3, wherein pressure gradient stresses are applied to said precursor material via sonic or hydrodynamic cavitation at temperatures below 80° C.

11. A nanonization method according to one of claims 1-3, wherein cooling is applied to said precursor material to embrittle and to reduce decomposition.

12. A nanonization method according to one of claims 1-3, wherein cooling before and during size-reduction is realized using liquid nitrogen.

13. A nanonization method according to claim 1, wherein scavenger molecules are added to reduce protein decomposition in the amount ranging from 0.01-2% by weight with respect to the precursor material.

14. A nanonization method according to claim 13, whereinthe scavenger molecules are alpha-tocopherol, naringenin, retinol, iodide, coenzyme Q10, melatonin, carotenoid terpenoids, flavonoid polyphenolics, phenolic acids and esters, glutathione, N-acetylcycleine, phytic acid, oxalic acid, citric acid, eugenol, xanthones, curcumin, flavonolignans, R-lipoic acid, uric acid, carotene, ubiquinol, ascorbic acid, butylated hydroxytoluene, bisulfite, and/or thiosulfate.

15. A nanonization method according to claim 1, wherein solid powders are added to facilitate the process of physical size reduction, the precursor, and said solid powder, being administered in a respective ratio ranging from 2:1 to 1:1000 by weight.

16. A nanonization method according to claim 15, wherein said solid powders are potassium iodide, sodium iodide, sodium chloride or any other alkali or alkaline earth salt, active carbon, silicon dioxide, aluminum oxide, titanium dioxide, chitin, keratin, and/or polyimide.

17. A nanonization method according to claim 1, wherein stabilizer molecules are added to prevent/restrict re-agglomeration in a 2-to-100 fold excess by weight.

18. A nanonization method according to claim 17, wherein the stabilizer molecules are potassium iodide, sodium iodide, sodium chloride, or any alkali or alkaline earth salt, ammonium salts, carbohydrates, polyols, polyvinylpyridine, polyvinylpyrolidone, polyamides, citric acid, ascorbic acid, albumin, hypromellose and/or gelatin.

19. A nanonization method according to claim 1, wherein mechanical shear forces are applied to said precursor material using a conventional high-shear mixer/compounding device operated at 1000-6000 rpm.

20. A nanonization method according to claim 1, wherein hydrodynamic shear stresses are applied to said precursor material in aqueous or organic media using a homogenizer as dispersing/mixing instrument operated at 1000-2000 rpm.

21. A nanonization method according to claim 1, wherein hydrodynamic shear stresses are applied to said precursor material from 30 min to 1.5 h at temperatures below 100° C.

* * * * *